United States Patent
Zhang et al.

(10) Patent No.: US 9,856,212 B1
(45) Date of Patent: Jan. 2, 2018

(54) BIPHENYL COMPOUNDS AND APPLICATIONS THEREOF

(71) Applicant: Shenyang Sinochem Agrochemicals R&D Co., Ltd., Shenyang, Liaoning (CN)

(72) Inventors: Lixin Zhang, Liaoning (CN); Jing Zhang, Liaoning (CN); Lanfeng Ban, Liaoning (CN); Hongfei Wu, Liaoning (CN); Yuquan Song, Liaoning (CN); Haibo Yu, Liaoning (CN); Peng Li, Liaoning (CN); Jingbo Xu, Liaoning (CN); Libao Xu, Liaoning (CN)

(73) Assignee: Shenyang Sinochem Agrochemicals R&D Co., Ltd., Shenyang, Liaoning (CN)

( * ) Notice: Subject to any disclaimer, the term of this patent is extended or adjusted under 35 U.S.C. 154(b) by 0 days.

(21) Appl. No.: 15/489,911

(22) Filed: Apr. 18, 2017

(51) Int. Cl.
*C07C 323/09* (2006.01)
*A01N 31/08* (2006.01)
*C07C 317/12* (2006.01)

(52) U.S. Cl.
CPC ............ *C07C 323/09* (2013.01); *A01N 31/08* (2013.01); *C07C 317/12* (2013.01)

(58) Field of Classification Search
CPC .............................. C07C 323/09; A01N 31/08
See application file for complete search history.

(56) References Cited

U.S. PATENT DOCUMENTS

2012/0053052 A1    3/2012   Gross et al.

FOREIGN PATENT DOCUMENTS

| | | |
|---|---|---|
| CN | 102341376 A | 2/2012 |
| CN | 103539681 A | 1/2014 |
| EP | 2403837 B1 | 12/2013 |
| JP | 2007145828 A | 6/2007 |
| JP | 2009023910 A | 2/2009 |
| JP | 2012519662 A | 8/2012 |
| TW | 201321347 A | 6/2013 |
| WO | 2010100189 A1 | 9/2010 |

*Primary Examiner* — Golam M M Shameem
(74) *Attorney, Agent, or Firm* — Suzannah K. Sundby, Esq.; Canady + Lortz LLP

(57) ABSTRACT

The present disclosure relates to acaricide, specifically to a kind of biphenyl compounds and uses thereof. The general formula I is as follows:

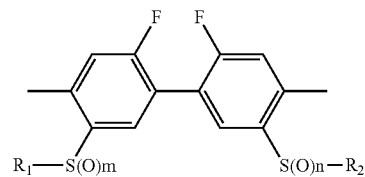

wherein: each substituent is defined as that in the description. The compounds of the general formula I show high acaricidal activities and can be used for controlling various harmful mites.

6 Claims, No Drawings

BIPHENYL COMPOUNDS AND APPLICATIONS THEREOF

FIELD OF THE INVENTION

The present disclosure relates to acaricide, specifically to a kind of biphenyl compounds and uses thereof.

BACKGROUND OF THE INVENTION

A wide range of research and applications on biphenyl compounds are carried out in the field of medicine. The compounds mainly used as insecticides and acaricides in the following general formula were disclosed in JP 2009023910A.

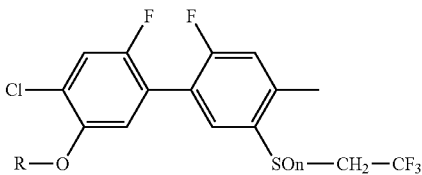

Neither the preparation of the biphenyl compounds represented by the structure of formula I, nor their insecticidal and acaricidal activities is described in state of the arts.

SUMMARY OF THE INVENTION

The purpose of the present disclosure is to provide a kind of biphenyl compounds controlling various harmful mites at very low dosage, and their applications for managing harmful mites in agriculture, forestry, or public health.

Detailed description of this invention is as follows:

The present disclosure provides a kind of biphenyl compounds as represented by the structure of formula I:

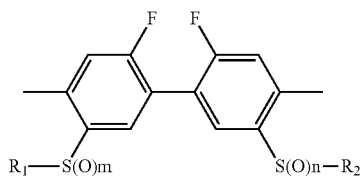

wherein:

$R_1$ and $R_2$ are independently selected from H, $C_1$-$C_8$ alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, cyano $C_1$-$C_8$ alkyl, or cyano $C_1$-$C_8$haloalkyl;

m and n are independently selected from 0, 1, or 2.

The preferred compounds of the general formula I in the present disclosure are:

$R_1$ and $R_2$ are independently selected from $C_1$-$C_8$haloalkyl, $C_2$-$C_8$haloalkenyl, $C_2$-$C_8$haloalkynyl, or cyano $C_1$-$C_8$haloalkyl. Further, $R_1$ and $R_2$ can be equally selected from $C_1$-$C_8$haloalkyl, $C_2$-$C_8$haloalkenyl, $C_2$-$C_8$haloalkynyl, or cyano $C_1$-$C_8$haloalkyl.

m and n are independently selected from 0, 1, or 2.

The further preferred compounds of the general formula I in the present disclosure are:

$R_1$ and $R_2$ are independently selected from $C_1$-$C_3$haloalkyl, $C_2$-$C_6$haloalkenyl, $C_2$-$C_6$haloalkynyl, or cyano $C_1$-$C_3$haloalkyl. Further, $R_1$ and $R_2$ can be equally selected from $C_1$-$C_3$haloalkyl, $C_2$-$C_6$haloalkenyl, $C_2$-$C_6$haloalkynyl, or cyano $C_1$-$C_3$haloalkyl.

m and n are independently selected from 0 or 1.

The more preferred compounds of the general formula I in the present disclosure are:

$R_1$ and $R_2$ are independently selected from trifluoromethyl, —$CH_2CF_3$, —$CH_2CHF_2$, —$CH_2CH_2F$, or —$CH$=$CF_2$. Further, $R_1$ and $R_2$ can be equally selected from trifluoromethyl, —$CH_2CF_3$, —$CH_2CHF_2$, —$CH_2CH_2F$, or —$CH$=$CF_2$.

m and n are independently selected from 0 or 1.

The most preferred compounds of the general formula I in the present disclosure are:

$R_1$ and $R_2$ are independently selected from —$CH_2CF_3$ or —$CH_2CHF_2$. Further, $R_1$ and $R_2$ can be equally selected from —$CH_2CF_3$ or —$CH_2CHF_2$.

m and n are independently selected from 0 or 1.

An application of the compounds of the general formula I for managing harmful mites in agriculture, forestry, or public health.

A composition with acaricidal activity, containing one or more compounds of the general formula I as active ingredient(s) and acceptable carrier in agriculture, the weight percentage of the active ingredient(s) in the composition is 0.1-99%.

In above definitions of the compounds of the general formula I, the term "alkyl" indicates linear or branched alkyl, such as methyl, ethyl, n-propyl, i-propyl, various isomers of butyl, pentyl and hexyl, cyclopropyl, cyclopentyl, cyclohexyl, or cyclopropylmethyl. "Haloalkyl" indicates linear or branched alkyl substituted by one or more halogen atoms that may be the same as or different from each other, such as monochloromethyl, dichloromethyl, trichloromethyl, monofluoromethyl, difluoromethyl, trifluoromethyl, perfluoropropan-2-yl. "alkenyl" indicates linear or branched alkenyl, such as vinyl, 1-propenyl, isopropyl, various isomers of butenyl, pentenyl and hexenyl, allyl, or 2,4-hexadienyl. "haloalkenyl" indicates linear or branched alkenyl substituted by one or more halogen atoms that may be the same as or different from each other. "alkynyl" indicates linear or branched alkynyl, such as ethynyl, 1-propargyl, various isomers of butynyl, pentynyl and hexynyl, or 2,5-hexydinyl. "haloalkynyl" indicates linear or branched alkynyl substituted by one or more halogen atoms that may be the same as or different from each other. "cyanoalkyl" indicates NC-alkyl, such as NC—$CH_2$— or NC—$CH_2$—$CH_2$—. "cyanohaloalkyl" indicates NC-haloalkyl, such as NC—CHBr— or NC—CHCl—CHCl—.

Some compounds of the general formula I may have one or more chiral centers, when they are the mixture of enantiomers or diastereoisomers. This invention provides single enantiomer, single diastereoisomer or the mixture of them, and their uses.

The specific compounds in Table 1 are used to illustrate the present invention, but not to limit it.

TABLE 1

I (structure: biphenyl with two F, two methyl, R$_1$—S(O)$_m$ and S(O)$_n$—R$_2$ substituents)

| Compound | R$_1$ | R$_2$ | m | n |
|---|---|---|---|---|
| 1 | CH$_2$CF$_3$ | CH$_2$CF$_3$ | 0 | 0 |
| 2 | CH$_2$CF$_3$ | CH$_2$CF$_3$ | 0 | 1 |
| 3 | CH$_2$CF$_3$ | CH$_2$CF$_3$ | 1 | 1 |
| 4 | CH$_2$CF$_3$ | CH$_2$CF$_3$ | 1 | 2 |
| 5 | CF$_3$ | CH$_2$CF$_3$ | 0 | 0 |
| 6 | CF$_3$ | CH$_2$CF$_3$ | 0 | 1 |
| 7 | CF$_3$ | CH$_2$CF$_3$ | 1 | 1 |
| 8 | CH$_3$ | CH$_2$CF$_3$ | 0 | 0 |
| 9 | CH$_3$ | CH$_2$CF$_3$ | 0 | 1 |
| 10 | CH$_3$ | CH$_2$CF$_3$ | 1 | 1 |
| 11 | CH$_2$CH$_3$ | CH$_2$CF$_3$ | 0 | 0 |
| 12 | CH$_2$CH$_3$ | CH$_2$CF$_3$ | 0 | 1 |
| 13 | CH$_2$CH$_3$ | CH$_2$CF$_3$ | 1 | 1 |
| 14 | cyclopropylmethyl | CH$_2$CF$_3$ | 0 | 0 |
| 15 | cyclopropylmethyl | CH$_2$CF$_3$ | 0 | 1 |
| 16 | cyclopropylmethyl | CH$_2$CF$_3$ | 1 | 1 |
| 17 | CH$_2$CH$_2$CF$_3$ | CH$_2$CF$_3$ | 0 | 0 |
| 18 | CH$_2$CH$_2$CF$_3$ | CH$_2$CF$_3$ | 0 | 1 |
| 19 | CH$_2$CH$_2$CF$_3$ | CH$_2$CF$_3$ | 1 | 1 |
| 20 | CH$_2$CClF$_2$ | CH$_2$CF$_3$ | 0 | 0 |
| 21 | CH$_2$CClF$_2$ | CH$_2$CF$_3$ | 0 | 1 |
| 22 | CH$_2$CClF$_2$ | CH$_2$CF$_3$ | 1 | 1 |
| 23 | CF$_2$CHF$_2$ | CH$_2$CF$_3$ | 0 | 0 |
| 24 | CF$_2$CHF$_2$ | CH$_2$CF$_3$ | 0 | 1 |
| 25 | CF$_2$CHF$_2$ | CH$_2$CF$_3$ | 1 | 1 |
| 26 | CF$_2$CHClF | CH$_2$CF$_3$ | 0 | 0 |
| 27 | CF$_2$CHClF | CH$_2$CF$_3$ | 0 | 1 |
| 28 | CF$_2$CHClF | CH$_2$CF$_3$ | 1 | 1 |
| 29 | CH$_2$CF$_2$CHF$_2$ | CH$_2$CF$_3$ | 0 | 0 |
| 30 | CH$_2$CF$_2$CHF$_2$ | CH$_2$CF$_3$ | 0 | 1 |
| 31 | CH$_2$CF$_2$CHF$_2$ | CH$_2$CF$_3$ | 1 | 1 |
| 32 | CH$_2$CF$_2$CF$_3$ | CH$_2$CF$_3$ | 0 | 0 |
| 33 | CH$_2$CF$_2$CF$_3$ | CH$_2$CF$_3$ | 0 | 1 |
| 34 | CH$_2$CF$_2$CF$_3$ | CH$_2$CF$_3$ | 1 | 1 |
| 35 | CF$_2$CHFCF$_3$ | CH$_2$CF$_3$ | 0 | 0 |
| 36 | CF$_2$CHFCF$_3$ | CH$_2$CF$_3$ | 0 | 1 |
| 37 | CF$_2$CHFCF$_3$ | CH$_2$CF$_3$ | 1 | 1 |
| 38 | CH$_2$CF$_2$CF$_2$CF$_3$ | CH$_2$CF$_3$ | 0 | 0 |
| 39 | CH$_2$CF$_2$CF$_2$CF$_3$ | CH$_2$CF$_3$ | 0 | 1 |
| 40 | CH$_2$CF$_2$CF$_2$CF$_3$ | CH$_2$CF$_3$ | 1 | 1 |
| 41 | CH$_2$CF$_2$CF$_2$CF$_2$CF$_3$ | CH$_2$CF$_3$ | 0 | 0 |
| 42 | CH$_2$CF$_2$CF$_2$CF$_2$CF$_3$ | CH$_2$CF$_3$ | 0 | 1 |
| 43 | CH$_2$CF$_2$CF$_2$CF$_2$CF$_3$ | CH$_2$CF$_3$ | 1 | 1 |
| 44 | CH$_2$CF$_2$CF$_2$CF$_2$CF$_2$CF$_3$ | CH$_2$CF$_3$ | 0 | 0 |
| 45 | CH$_2$CF$_2$CF$_2$CF$_2$CF$_2$CF$_3$ | CH$_2$CF$_3$ | 0 | 1 |
| 46 | CH$_2$CF$_2$CF$_2$CF$_2$CF$_2$CF$_3$ | CH$_2$CF$_3$ | 1 | 1 |
| 47 | CH$_2$CH$_2$CH$_3$ | CH$_2$CF$_3$ | 0 | 0 |
| 48 | CH$_2$CH$_2$CH$_3$ | CH$_2$CF$_3$ | 0 | 1 |
| 49 | CH$_2$CH$_2$CH$_3$ | CH$_2$CF$_3$ | 1 | 1 |
| 50 | 3,4,4-trifluorobut-3-en-1-yl | CH$_2$CF$_3$ | 0 | 0 |
| 51 | 3,4,4-trifluorobut-3-en-1-yl | CH$_2$CF$_3$ | 0 | 1 |
| 52 | 3,4,4-trifluorobut-3-en-1-yl | CH$_2$CF$_3$ | 1 | 1 |
| 53 | CH$_2$CH$_2$CH$_2$CH$_3$ | CH$_2$CF$_3$ | 0 | 0 |
| 54 | CH$_2$CH$_2$CH$_2$CH$_3$ | CH$_2$CF$_3$ | 0 | 1 |
| 55 | CH$_2$CH$_2$CH$_2$CH$_3$ | CH$_2$CF$_3$ | 1 | 1 |
| 56 | CH$_2$CHF$_2$ | CH$_2$CF$_3$ | 0 | 0 |
| 57 | CH$_2$CHF$_2$ | CH$_2$CF$_3$ | 0 | 1 |
| 58 | CH$_2$CHF$_2$ | CH$_2$CF$_3$ | 1 | 1 |
| 59 | CH$_2$CH$_2$F | CH$_2$CF$_3$ | 0 | 0 |
| 60 | CH$_2$CH$_2$F | CH$_2$CF$_3$ | 0 | 1 |
| 61 | CH$_2$CH$_2$F | CH$_2$CF$_3$ | 1 | 1 |
| 62 | CH$_2$CHF$_2$ | CH$_2$CHF$_2$ | 0 | 0 |
| 63 | CH$_2$CHF$_2$ | CH$_2$CHF$_2$ | 0 | 1 |
| 64 | CH$_2$CHF$_2$ | CH$_2$CHF$_2$ | 1 | 1 |

$^1$H NMR (300 MHz, CDCl$_3$) data of some representative compounds are as follows:

Compound 1: δ (ppm): 2.53 (s, 6H), 3.35 (q, 4H), 7.05-7.09 (m, 2H), 7.53-7.56 (m, 2H).

Compound 2: δ (ppm): 2.45 (s, 3H), 2.54 (s, 3H), 3.34 (q, 2H), 3.48 (q, 2H), 7.07-7.12 (m, 2H), 7.58 (d, 1H), 7.99 (d, 1H).

Compound 3: δ (ppm): 2.46 (s, 3H), 2.49 (s, 3H), 3.97-4.08 (m, 4H), 7.30-7.32 (m, 2H), 7.93-7.95 (m, 2H).

Compound 62: δ (ppm): 2.50 (s, 6H), 3.05-3.20 (m, 4H), 5.65-6.06 (m, 2H), 7.04-7.07 (m, 2H), 7.46-7.49 (m, 2H).

Compound 63: δ (ppm): 2.42 (s, 3H), 2.46 (s, 3H), 3.31-3.64 (m, 4H), 5.90-6.70 (m, 2H), 7.22 (d, 1H), 7.28 (d, 1H), 7.60 (d, 1H), 7.83 (d, 1H).

The compounds of general formula I in the present disclosure can be prepared by the following methods, unless further specification, the substituents in the reaction schemes are the same as above definitions:

Method 1 (For preparing the compounds of the general formula I when R$_1$=R$_2$ and m=n=0. R=R$_1$=R$_2$ in the following scheme.)

(Scheme: Intermediate II (aminothiophenol with F and methyl substituents) → III (R—S substituted aniline) → IV (R—S substituted iodobenzene) → I-1 (biphenyl product with two R—S groups))

Intermediate II and appropriate halogenating agent are reacted in appropriate solvent to yield the compounds of the general formula III at a certain temperature from 0° C. to boiling point for 30 minutes to 48 hours with the presence of appropriate base. The appropriate halogenating agent is selected from iodomethane, iodoethane, 2,2,2-trifluoroiodoethane, cyclopropyl bromide, chloroacetonitrile, vinyl bromide, propargyl bromide, dibromoacetonitrile, 2-bromo-1,1-difluoroethene, 1,2-dibromoethyne, etc. The appropriate solvent is selected from water, dichloromethane, chloroform, carbon tetrachloride, hexane, benzene, toluene, acetonitrile, tetrahydrofuran, dioxane, N,N-dimethylformamide, dimethyl sulfoxide, etc. The appropriate base is selected from potassium hydroxide, sodium hydroxide, potassium carbonate, sodium carbonate, sodium bicarbonate, triethylamine, pyridine, sodium methoxide, sodium ethoxide, sodium hydride, potassium tert-butoxide, sodium tert-butoxide, etc.

The compounds of the general formula III, sodium nitrite, one or more of acids and potassium iodide are reacted in appropriate solvent to yield the compounds of the general formula IV at a certain temperature from 0° C. to 100° C. for 30 minutes to 48 hours. Acid is selected from inorganic acid or organic acid, such as hydrochloric acid, hydrobromic acid, sulfuric acid, phosphoric acid, formic acid, acetic acid, propanoic acid, butyric acid, valeric acid, trifluoroacetic acid, oxalic acid, malonic acid, methanesulfonic acid, etc. The appropriate solvent is selected from water, chloroform, dichloromethane, carbon tetrachloride, hexane, benzene, toluene, ethyl acetate, N,N-dimethylformamide, tetrahydrofuran, dioxane, etc.

The compounds of the general formula IV and bis(pinacolato)diboron are reacted in appropriate solvent to yield the compounds of general formula I-1 at a certain temperature from 0° C. to boiling point for 30 minutes to 48 hours with the presence of appropriate base and palladium catalyst. The appropriate solvent is selected from water, dichloromethane, chloroform, carbon tetrachloride, hexane, benzene, toluene, acetonitrile, tetrahydrofuran, dioxane, N,N-dimethylformamide, dimethyl sulfoxide, etc. The appropriate base is selected from alkali metal hydrides, hydroxides, or carbonates, such as sodium hydride, potassium hydride, sodium hydroxide, potassium hydroxide, sodium carbonate, potassium carbonate and cesium carbonate, or organic base, such as triethylamine, sodium tert-butoxide and potassium tert-butoxide. The appropriate palladium catalyst is selected from tetrakis(triphenylphosphine)palladium or [1,1'-Bis(diphenylphosphino)ferrocene]dichloro-palladium(II), etc., the appropriate ligand such as 1,1'-Bis(diphenylphosphino)ferrocene, triphenylphosphine and tri-t-butyl phosphine, can be added with it in some case.

Method 2 (For preparing the compounds of the general formula I when m=n=0, and $R_1$ is the same as or different from $R_2$.)

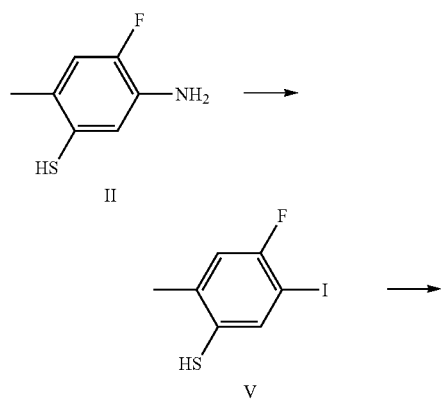

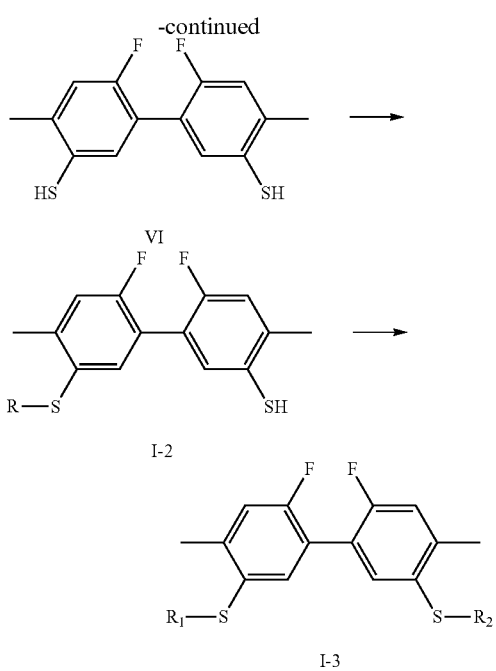

Intermediate II, sodium nitrite, one or more of acids and potassium iodide are reacted in appropriate solvent to yield the compounds of the general formula V at a certain temperature from 0° C. to 100° C. for 30 minutes to 48 hours. Acid is selected from inorganic acid or organic acid, such as hydrochloric acid, hydrobromic acid, sulfuric acid, phosphoric acid, formic acid, acetic acid, propanoic acid, butyric acid, valeric acid, trifluoroacetic acid, oxalic acid, malonic acid, methanesulfonic acid, etc. The appropriate solvent is selected from water, chloroform, dichloromethane, carbon tetrachloride, hexane, benzene, toluene, ethyl acetate, N,N-dimethylformamide, tetrahydrofuran, dioxane, etc.

The compounds of the general formula V and bis(pinacolato)diboron are reacted in appropriate solvent to yield intermediate VI at a certain temperature from −10° C. to boiling point for 30 minutes to 48 hours with the presence of appropriate base and palladium catalyst. The appropriate solvent is selected from water, dichloromethane, chloroform, carbon tetrachloride, hexane, benzene, toluene, acetonitrile, tetrahydrofuran, dioxane, N,N-dimethylformamide, dimethyl sulfoxide, etc. The appropriate base is selected from alkali metal hydrides, hydroxides, or carbonates, such as sodium hydride, potassium hydride, sodium hydroxide, potassium hydroxide, sodium carbonate, potassium carbonate and cesium carbonate, or organic base, such as triethylamine, sodium tert-butoxide and potassium tert-butoxide. The appropriate palladium catalyst is selected from tetrakis(triphenylphosphine)palladium or [1,1'-Bis(diphenylphosphino)ferrocene]dichloropalladium(II), etc., the appropriate ligand such as 1,1'-Bis(diphenylphosphino)ferrocene, triphenylphosphine and tri-t-butyl phosphine, can be added with it in some case.

Intermediate VI and appropriate halogenating agent are reacted in appropriate solvent to yield the compounds of general formula I-2 at a certain temperature from 0° C. to boiling point for 30 minutes to 48 hours with the presence of appropriate base. The compounds of the general formula I-2 are further reacted to yield the compounds of the general formula I-3 at the same reaction conditions. The appropriate halogenating agent is selected from iodomethane, iodoethane, 2,2,2-trifluoroiodoethane, cyclopropyl bromide, chloroacetonitrile, vinyl bromide, propargyl bromide, dibromoacetonitrile, 2-bromo-1,1-difluoroethene, 1,2-dibromoethyne, etc.

The appropriate solvent is selected from water, dichloromethane, chloroform, carbon tetrachloride, hexane, benzene, toluene, acetonitrile, tetrahydrofuran, dioxane, N,N-dimethylformamide, dimethyl sulfoxide, etc. The appropriate base is selected from potassium hydroxide, sodium hydroxide, potassium carbonate, sodium carbonate, sodium bicarbonate, triethylamine, pyridine, sodium methoxide, sodium ethoxide, sodium hydride, potassium tert-butoxide, sodium tert-butoxide, etc.

Method 3 (For preparing the compounds of general formula I when m and n are independently selected from 0, 1, or 2, but not m=n=0.)

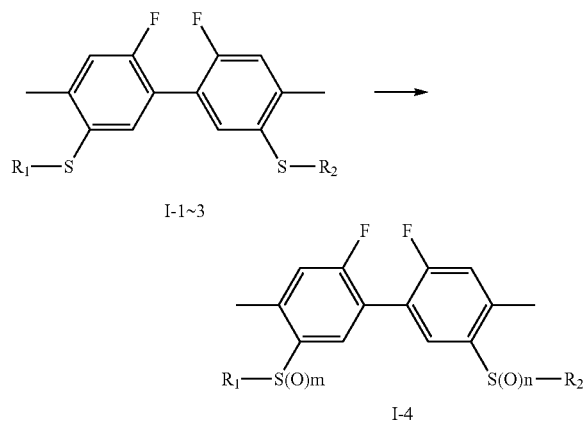

I-1~3

I-4

The compounds of the general formula I-1, I-2, and I-3, and appropriate oxidant are reacted in appropriate solvent to yield the compounds of the general formula I-4 as the sulfoxides or sulfones at a certain temperature from 0° C. to 100° C. for 10 minutes to 48 hours with the presence of appropriate base. The appropriate oxidant is selected from 3-chloroperbenzoic acid, hydrogen peroxide, or sodium periodate, etc. The appropriate solvent is selected from water, methanol, ethanol, ether, dichloromethane, chloroform, carbon tetrachloride, hexane, benzene, toluene, ethyl acetate, N, N-dimethylformamide, tetrahydrofuran, dioxane, etc. The preferred reaction temperature is from 20° C. to 40° C.

The acquisitions of the starting materials and intermediates mentioned above are as follows: Intermediate II can be prepared according to the procedures disclosed in the WO2010100189, US2012053052, JP2012519662, EP2403837 and CN102341376.

The conventional starting materials and agents such as halogenating agent, sodium nitrite, inorganic acid, organic acid, potassium iodide, bis(pinacolato)diboron, palladium catalyst, ligand and oxidant, are commercially available, or can be prepared according to the conventional procedures.

Because the compounds of the general formula I in the present disclosure possess surprisingly acarididal activity, especially against important species of tetranychidae (*Tetranychusurticae, Tetranychuscinnabarinus, Panonychusulmi, Panonychuscitri*, etc.), eriophyidae, tarsonemidae, etc., this invention also provides the application of the compounds of the general formula I for controlling harmful mites.

The compounds mentioned above can be advantageously used in protecting crops of farming and gardening, domestic and breeding animals and the environments frequented by human beings from harmful mites because of their positive characteristics.

In order to obtain the desired effect, the dosage of compounds to be applied can vary with various factors such as the compound used, the crop to be protected, the species of harmful organism, the degree of infestation, the climatic conditions, the application method and the formulation adopted.

Doses of compound ranging from 10 g to 5 kg per hectare generally provide a sufficient control to harmful mites.

The present disclosure also aims to provide a method of controlling harmful mites in crops of farming and gardening and/or on domestic and breeding animals and/or in environments frequented by human beings, by the application of the compounds of the general formula I. In particular, the dosage of compound to be applied varies from 10 g to 5 kg per hectare.

For practical application in agriculture, it is usually useful to apply compositions containing one or more compounds of the general formula I.

Therefore a technical object of the present disclosure also relates to acaricidal compositions containing one or more compounds of the general formula I as active ingredient(s) and acceptable carrier in agriculture, the weight percentage of the active ingredient(s) in the composition is 0.1-99%.

Compositions can be used in the form of dry powders, wettable powders, emulsifiable concentrates, microemulsions, pastes, granulates, solutions, suspensions, etc. The selection of the type of composition depends on the specific application.

The compositions are prepared in the known way, for example by diluting or dissolving the active substance with a solvent medium and/or a solid diluent, optionally in the presence of surface-active agents.

Solid diluents or carriers which can be used are silica, kaolin, bentonite, talc, diatomite, dolomite, calcium carbonate, magnesia, chalk, clays, synthetic silicates, attapulgite, seppiolite and so on.

Besides water, liquid diluents which can be used are aromatic organic solvents (xylols or mixtures of alkylbenzols, chlorobenzene, etc.), paraffins (petroleum fractions), alcohols (methanol, propanol, butanol, octanol, glycerin), esters (ethyl acetate, isobutyl acetate, etc.), ketones (cyclohexanone, acetone, acetophenone, isophorone, ethylamylketone, etc.), amides (N,N-dimethylformamide, N-methylpyrrolidone, etc.).

Surface-active agents which can be used are salts of sodium, calcium, triethylamine or triethanolamine of alkylsulfonates, alkylarylsulfonates, polyethoxylatedalkylphenols, polyethoxylated esters of sorbitol, ligninsulfonates, etc.

The compositions can also contain special additives for particular purposes, for example adhesion agents such as Arabic gum, polyvinyl alcohol and polyvinyl-pyrrolidone.

The concentration of active ingredient in the above compositions can vary within a wide range depending on the active compound, the applications for which they are destined, the environmental conditions and the type of adopted formulation. In general the concentration of active ingredient ranges from 1 to 90%, preferably from 5 to 50%.

DETAILED DESCRIPTION OF THE INVENTION

The following examples are illustrative of the present invention, but without being restricted thereby. (All the starting materials are commercially available except special explanation.)

PREPARATION EXAMPLE

Example 1: The Preparation of Compound 1

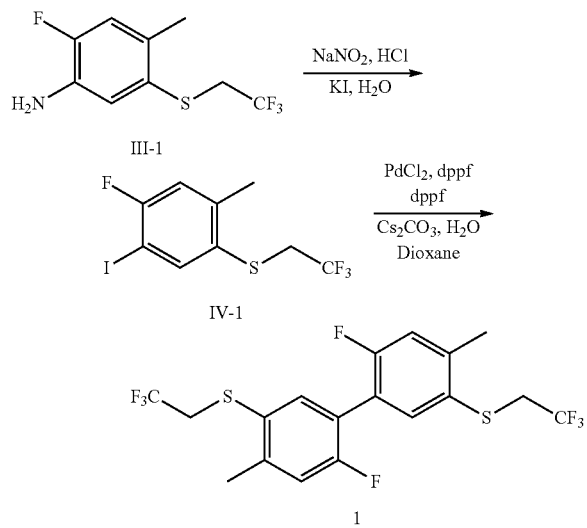

1.1 the Preparation of Intermediate IV-1

To 10.00 g (41.80 mmol) of 2-fluoro-4-methyl-5-((2,2,2-trifluoroethyl)thio)aniline (Intermediate III-1, can be prepared according to the procedures disclosed in the WO2010100189, US2012053052, JP2012519662, EP2403837 and CN102341376) in a 500 mL flask was added concentrated hydrochloric acid (60 ml). The mixture was cooled and stirred for 30 minutes at 0-5° C. To the mixture was added dropwise a 100 ml solution of sodium nitrite (3.46 g, 50.15 mmol) in water at 0-5° C. The reaction mixture was stirred for an hour. To the reaction mixture was added dropwise a 100 ml solution of potassium iodide (13.88 g, 83.61 mmol) in water at 0-5° C. The resulting mixture was stirred for 3 hours at room temperature. After the reaction was over by Thin-Layer Chromatography monitoring, to the resulting mixture was added ethyl acetate (300 ml). The organic layer was washed by water (200 ml) and saturated brine (200 ml) in turn, dried over anhydrous magnesium sulfate, filtered and concentrated under reduced pressure. The crude product was purified by column chromatography on silica gel (eluent: ethyl acetate/petroleum ether (boiling point range 60-90° C.)=1/30 (volume ratio)) to yield the title compound (8.79 g) as an oil.

1.2 the Preparation of Compound 1

A mixture of (4-fluoro-5-iodo-2-methylphenyl)(2,2,2-trifluoroethyl)sulfane (intermediate IV-1, 5.00 g, 14.28 mmol), bis(pinacolato)diboron (5.44 g, 21.42 mmol), cesium carbonate (9.32 g, 28.60 mmol), [1,1'-Bis(diphenylphosphino)ferrocene]dichloropalladium(II) (0.06 g), 1,1'-Bis(diphenylphosphino)ferrocene (0.04 g), 1,4-dioxane (100 ml) and water (3 ml) was refluxed for 3 hours. After the reaction was over by Thin-Layer Chromatography monitoring, to the mixture was added ethyl acetate (200 ml). The organic layer was washed by water (100 ml) and saturated brine (100 ml) in turn, dried over anhydrous magnesium sulfate, filtered and concentrated under reduced pressure. The crude product was purified by column chromatography on silica gel (eluent: ethyl acetate/petroleum ether (boiling point range 60-90° C.)=1/30 (volume ratio)) to yield the title compound (4.79 g) as a white solid (melting point: 59-60° C.).

$^1$H NMR spectrum (300 MHz, internal standard: TMS, solvent: CDCl$_3$) δ (ppm): 2.53 (s, 6H), 3.35 (q, 4H), 7.05-7.09 (m, 2H), 7.53-7.56 (m, 2H). LC-MS (m/z): 446.9 (m+1).

Example 2: The Preparation of Compound 2 and 3

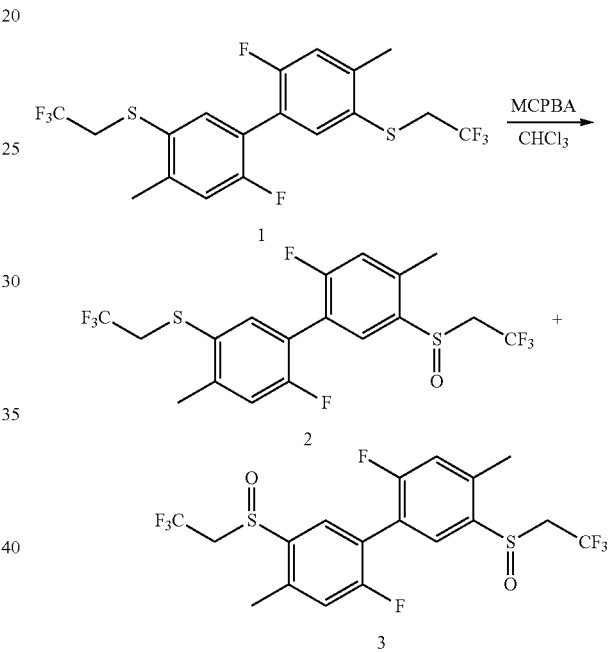

To compound 1 (2.00 g, 4.48 mmol) in chloroform (20 ml) was added 3-chloroperbenzoic acid (MCPBA) (85%, 0.98 g, 4.68 mmol) in three batches at 0-5° C. The mixture was stirred at 0-5° C. for 2 hours. After the reaction was over by Thin-Layer Chromatography monitoring, the mixture was washed by sodium subsulfite aqueous solution and sodium bicarbonate aqueous solution in turn, dried over anhydrous magnesium sulfate, filtered and concentrated under reduced pressure. The crude product was purified by column chromatography on silica gel (eluent: ethyl acetate/petroleum ether (boiling point range 60-90° C.)=1/6-1/3 (volume ratio)) to yield the title compound 2 (1.21 g) as a white solid and the title compound 3 (0.70 g) as a white solid.

Compound 2: $^1$H NMR spectrum (300 MHz, internal standard: TMS, solvent: CDCl$_3$) δ (ppm): 2.45 (s, 3H), 2.54 (s, 3H), 3.34 (q, 2H), 3.48 (q, 2H), 7.07-7.12 (m, 2H), 7.58 (d, 1H), 7.99 (d, 1H). LC-MS (m/z): 463.0 (m+1).

Compound 3: $^1$H NMR spectrum (300 MHz, internal standard: TMS, solvent: CDCl$_3$) δ (ppm): 2.46 (s, 3H), 2.49 (s, 3H), 3.97-4.08 (m, 4H), 7.30-7.32 (m, 2H), 7.93-7.95 (m, 2H). LC-MS (m/z): 479.0 (m+1).

Other compounds of general formula I (When $R_1$=$R_2$) in the present disclosure were prepared according to the above examples. More specifically, according to Method 1 mentioned above, the reagents were changed to obtain the targets. Other compounds of general formula I (When $R_1$ is different from $R_2$) in the present disclosure were prepared according to Method 2 mentioned above, by using the different halogenating agent.

Biological Testing

Example 3: Determination of Acaricidal Activity in Greenhouse

According to the solubility of test compounds, the compounds are dissolved in acetone or dimethyl sulfoxide, and then diluted with 0.1% aqueous solution of Tween 80 to form 50 ml test liquid, the content of acetone or dimethyl suloxide in the total solution is not more than 10%.

3.1 Test Against Adult Spider Mite (*Tetranychuscinnabarinus*)

The adult spider mites (*Tetranychuscinnabarinus*) were put into two true leaves of bean plants. After the number of mites were investigated, the solution of certain concentrations of test compounds was sprayed by using a sprinkler. Three replicates were set for each treatment. Then the leaves were maintained in standard observation room. After 72 h the survival mites in each leaf were observed, and mortality of the mites was determined.

According to above method, the representative compounds of this invention were tested against adult spider mites. Some test results were listed in Table 2.

TABLE 2

Acaricidal activity data against adult spider mites (mortality, %)

| Compound | Mortality (%) | |
|---|---|---|
| | 100 mg/L | 5 mg/L |
| Compound 1 | 100 | 100 |
| Compound 2 | 100 | / |
| Compound 3 | 100 | / |
| Compound 62 | 100 | / |
| Compound 63 | 100 | / |

Note:
"/" stands for no data.

The above table showed the compounds of general formula I in the present disclosure were acaricidal. Compound 1 was taken as an example to be further tested as follows.

3.2 Test Against Deutonymph of Spider Mite (*Tetranychuscinnabarinus*)

Ten healthy female adult spider mites (*Tetranychuscinnabarinus*) were put into two true leaves of bean plants. The adult spider mites were removed after 24 h and the eggs were to be continued incubating. After ten days, the number of deutonymph were investigated and recorded. The solution of certain concentrations of test compounds was sprayed by using a sprinkler. Three replicates were set for each treatment. Then the deutonymph of spider mites were maintained in standard observation room. After 72 h, the survival mites in each leaf were observed, and mortality of the mites was determined.

According to above method, high acaricidal compound 1 in this invention and commercial product 95% pyridaben TC were parallel tested against deutonymph of spider mite. The test results were listed in Table 3.

TABLE 3

Acaricidal activity data against deutonymph of spider mites (mortality, %)

| Compound | Mortality (%) | | |
|---|---|---|---|
| | 1 mg/L | 0.5 mg/L | 0.25 mg/L |
| Compound 1 | 100 | 97 | 64 |
| pyridaben | 84 | 60 | 25 |

3.3 Test Against Egg of Spider Mite (*Tetranychuscinnabarinus*)

Two true leaves of bean plants were taken and one true leaf was removed. Then ten healthy female adult spider mites were put into the true leaf. The adult spider mites were removed after 24 h and the eggs were investigated. The solution of certain concentrations of test compounds was sprayed by using a sprinkler. Three replicates were set for each treatment. The untreated eggs were all incubated after 5 days. The unincubation of treated eggs in leaf was observed, and incubation inhibition rate of the eggs was determined.

According to above method, high acaricidal compound 1 in this invention and commercial product 98% spirodiclofen TC were parallel tested against eggs of spider mites. The test results were listed in Table 4.

TABLE 4

Acaricidal activity data against eggs of spider mites (incubation inhibition rate, %)

| Compound | Incubation inhibition rate (%) | | |
|---|---|---|---|
| | 5 mg/L | 1 mg/L | 0.25 mg/L |
| Compound 1 | 100 | 34 | 18 |
| spirodiclofen | 100 | 37 | 13 |

3.4 Test of Systemic Activity Against Spider Mite Through Root Absorption

The high acaricidal compound 1 were dissolved in acetone, and then diluted with 0.1% aqueous solution of Tween 80 to form test solution in different concentration. Three replicates were set for each treatment. Water is blank control. The 10 ml compound 1 solution was added into the tube. Two true leaves bean plants were taken and the soil in the root was removed. The bean plant was dipped into the test solution in different concentration. After absorbing 24 h, 30 to 50 spider mites were put onto the true leaves. Then the bean plants were maintained in observation room at 25±1° C. After 72 h, the death and survival mites in each leaf was observed, the mortality of the mites and systemic activity was determined. The test results were listed in Table 5.

TABLE 5

Systemic activity against spider mites of compound 1 through root absorption (mortality, %)

| Compound | Mortality (%) | |
| --- | --- | --- |
| | 200 mg/L | 50 mg/L |
| Compound 1 | 88 | 80 |

Example 4: Field Trial

Field Trial Against Citrus Red Mite (*Panonychuscitri*) (Jiangxi, China)

The trial was carried out in a 2-year-old Shatang orange orchard in Ganzhou city Jiangxi province, trifoliate orange trees were selected as stocks, the intervals between two plants was 1.50×2.50 m, the average height was 1.45 m and the crown width was 1.30 m. Two trees were selected in each plot, with random arrangement and 4 replications. Compound 1 (10% SC) was set at three different doses (100 mg/L, 50 mg/L and 25 mg/L), spirodiclofen (29% SC) was set at one dose (50 mg/L), and pyridaben (20% EC) was set at one dose (100 mg/L). MatabiSupergreen 16 Knapsack Sprayer 16 Liter was used to spray evenly with 2 L of spraying volume for each plant. The plants were treated once in May at that time, adults, nymphs, eggs of citrus red mite all existed, with adults/eggs=1/1.2. During the day the plants were treated, and the weather was good with the average temperature at 24° C. The first three days after treatment were all clear days. The number of mites was investigated before treatment and on the 1st, 3rd, 7th, 14th, 22nd and 28th day after treatment respectively. Two trees of each plot were investigated according to the five directions of the tree crown (east, south, west, north and central), 5 leaves in each direction were investigated to calculate the number of living mites, with 50 leaves each plot. The decline rate of mite population and corrected efficacy were calculated according to formulas below:

The decline rate of mite population (%)=[(the average number of mite on each leaf before treatment−the average number of mite on each leaf after treatment)/the average number of mite on each leaf before treatment]×100.

Corrected efficacy (%)=[(the decline rate of mite population in treated area−the decline rate of mite population in untreated area)/(100−the decline rate of mite population in untreated area)]×100.

The field trial results for compound 1 against citrus red mite (Ganzhou Jiangxi) were listed in Table 6.

TABLE 6

Field trial results for compound 1 against citrusred mite in Jiangxi

| Compound | Concentrations (mg/L) | Corrected efficacy (%) | | | | | |
| --- | --- | --- | --- | --- | --- | --- | --- |
| | | The 1st day after treatment | The 3rd day after treatment | The 7th day after treatment | The 14th day after treatment | The 22nd day after treatment | The 28th day after treatment |
| Compound 1 | 25 | 9 | 53 | 74 | 77 | 75 | 73 |
| | 50 | 18 | 87 | 92 | 91 | 92 | 92 |
| | 100 | 25 | 89 | 97 | 99 | 99 | 98 |
| spirodiclofen | 50 | 20 | 48 | 63 | 80 | 71 | 70 |
| pyridaben | 100 | 0 | 65 | 90 | 93 | 92 | 95 |

The other compounds of general formula I in the present disclosure, prepared by the methods mentioned above, showed corresponding bioefficacy.

We claim:

1. A biphenyl compound represented by formula I:

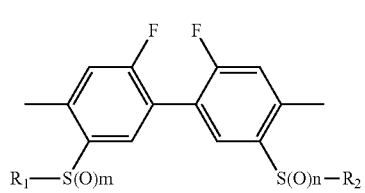

wherein:
   $R_1$ and $R_2$ are independently selected from H, $C_1$-$C_8$ alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, cyano $C_1$-$C_8$ alkyl, or cyano $C_1$-$C_8$haloalkyl;
   m and n are independently selected from 0, 1, or 2.

2. The compound according to the claim 1, wherein
   $R_1$ and $R_2$ are independently selected from $C_1$-$C_8$haloalkyl, $C_2$-$C_8$haloalkenyl, $C_2$-$C_8$haloalkynyl, or cyano $C_1$-$C_8$haloalkyl;
   m and n are independently selected from 0, 1, or 2.

3. The compound according to the claim 2, wherein
   $R_1$ and $R_2$ are independently selected from $C_1$-$C_3$haloalkyl, $C_2$-$C_6$haloalkenyl, $C_2$-$C_6$haloalkynyl, or cyano $C_1$-$C_3$haloalkyl;
   m and n are independently selected from 0 or 1.

4. The compound according to the claim 3, wherein
   $R_1$ and $R_2$ are independently selected from trifluoromethyl, —$CH_2CF_3$, —$CH_2CHF_2$, —$CH_2CH_2F$, or —CH=$CF_2$;
   m and n are independently selected from 0 or 1.

5. A method of controlling harmful mites in agriculture, forestry, or public health, which comprises applying the compound of claim 1 as an insecticide or an acaricide.

6. An acaricidal composition, comprising the compound according to claim 1 as an active ingredient and acceptable carrier in agriculture, wherein the weight percentage of the active ingredient(s) in the composition is 0.1-99%.

* * * * *